United States Patent [19]

Ishitani et al.

[11] 4,306,957

[45] Dec. 22, 1981

[54] DEVICE FOR PRODUCING CONTROL SIGNAL FOR FEEDBACK CONTROL OF AIR/FUEL RATIO

[75] Inventors: Shigeo Ishitani, Yokosuka; Shinji Kimura, Yokohama; Hiroshi Takao, Kamakura; Masaaki Uchida, Yokohama, all of Japan

[73] Assignee: Nissan Motor Co., Ltd., Yokohama, Japan

[21] Appl. No.: 172,228

[22] Filed: Jul. 25, 1980

[30] Foreign Application Priority Data

Jul. 28, 1979 [JP] Japan .................. 54-95575

[51] Int. Cl.³ .......................... G01N 27/58
[52] U.S. Cl. ............................ 204/195 S
[58] Field of Search ............ 204/195 S, 1 S; 123/440, 489; 60/276

[56] References Cited

U.S. PATENT DOCUMENTS

| | | | |
|---|---|---|---|
| 3,915,830 | 10/1975 | Isenberg | 204/195 S |
| 4,107,019 | 8/1978 | Takao et al. | 204/195 S |
| 4,126,532 | 11/1978 | Takao et al. | 204/195 S |
| 4,207,159 | 6/1980 | Kimura et al. | 204/195 S |
| 4,224,113 | 9/1980 | Kimura et al. | 204/1 T |

FOREIGN PATENT DOCUMENTS 2718907 11/1978 Fed. Rep. of Germany .
2350598 2/1977 France .

Primary Examiner—G. L. Kaplan
Attorney, Agent, or Firm—Schwartz, Jeffery, Schwaab, Mack, Blumenthal & Koch

[57] ABSTRACT

A device comprising an oxygen-sensitive element to be disposed in a combustion gas exhausted from a combustor to detect deviation of actual air/fuel ratio from a stoichiometric ratio. The element is a combination of two oxygen concentration cells each having a solid electrolyte layer, a measurement electrode layer formed on one side of the electrolyte layer, a reference electrode layer formed on the opposite side and covered with a shield layer. Either measurement electrode layers or reference electrode layers of the two cells are connected to each other, and a constant DC voltage is applied to the element to force a current to flow through solid electrolyte layers of both cells to cause migration of oxygen ions therethrough, from the measurement electrode to the reference electrode in one cell and reversely in the other. The device has a circuit to make a comparison between a fixed reference voltage and an output voltage developed between the measurement and reference electrodes of one cell of the element to produce a high-or-low level control signal according to the result of the comparison. The output voltage is independent of the internal resistance of the element and is scarcely affected by the temperature of the element.

16 Claims, 26 Drawing Figures

DEVICE FOR PRODUCING CONTROL SIGNAL FOR FEEDBACK CONTROL OF AIR/FUEL RATIO

BACKGROUND OF THE INVENTION

This invention relates to a device for producing a control signal for feedback control of the air/fuel ratio of an air-fuel mixture supplied to a combustor, such as the combustion chambers of an internal combustion engine, based on the concentration of oxygen in a combustion gas exhausted from the combustor.

In recent internal combustion engines, particularly in automotive engines, there has been developed a marked tendency to very minutely control the air/fuel mixing ratio to improve the efficiencies of the engines and reduce the emission of noxious components of exhaust gas. In many cases it is desired to feed an engine with a stoichiometrical air-fuel mixture, and it has already been put into practice to perform feedback control of air/fuel mixing ratio with the aim of maintaining a stoichiometric air/fuel ratio by using an exhaust gas sensor which provides a feedback signal indicative of the composition of an air-fuel mixture actually supplied to the engine.

For example, in an automotive engine system using a so-called three-way catalyst which can catalyze both reduction of nitrogen oxides and oxidation of carbon monoxide and unburned hydrocarbons contained in the exhaust gas, it is quite important to feed the engine always with an exactly stoichiometrical air-fuel mixture because this catalyst fully exhibits its ability in an exhaust gas produced by combustion of a stoichiometrical air-fuel mixture. Accordingly, in this engine system it becomes indispensable to perform feedback control of the air/fuel mixing ratio.

Usually, conventional feedback air/fuel ratio control systems aiming at a stoichiometric air/fuel ratio utilize an oxygen sensor that operates on the principle of concentration cell as an exhaust gas sensor to provide a feedback signal. This type of oxygen sensor has a layer of an oxygen ion conductive solid electrolyte, such as zirconia stabilized with calcia, formed into the shape of a tube closed at one end, a measurement electrode layer porously formed on the outer side of the solid electrolyte tube and a reference electrode layer formed on the inner side of the tube. When there is a difference in oxygen partial pressure between the reference electrode side and measurement electrode side of the solid electrolyte layer, this sensor generates an electromotive force between the two electrode layers. As an exhaust gas sensor, the measurement electrode layer is exposed to an engine exhaust gas while the reference electrode layer on the inside is exposed to atmospheric air utilized as the source of a reference oxygen partial pressure. In this state the magnitude of an electromotive force generated by this oxygen sensor exhibits a great and sharp change between a maximally high level and a minimally low level upon the occurrence of a change in the air/fuel ratio of a mixture fed to the engine across the stoichiometric air/fuel ratio. Accordingly it is possible to produce a fuel feed rate control signal based on the result of a comparison of the output of the oxygen sensor with a reference voltage which is set at the middle of the high and low levels of the sensor output.

However, this type of oxygen sensor has disadvantages such as significant temperatures dependence of its output characteristic, necessity of using a reference gas such as air, difficulty in reducing the size and insufficiency of mechanical strength.

To eliminate these disadvantages, U.S. patent application Ser. No. 12,763 filed Feb. 16, 1979 and now U.S. Pat. No. 4,207,159 discloses an advanced oxygen sensor, which is of a concentration cell type having a flat solid electrolyte layer with reference and measurement electrode layers formed respectively on the two opposite sides thereof and a shield layer formed on the reference electrode side of the solid electrolyte layer so as to cover the reference electrode layer entirely. Either the shield layer or the solid electrolyte layer is made rigid and thick enough to serve as a substrate, and each of the remaining three layers can be formed as a thin film-like layer. This sensor does not use any reference gas. Instead, a DC power supply is connected to this sensor so as to force a current to flow through the solid electrolyte layer between the reference and measurement electrode layers thereby to cause migration of oxygen ions through the solid electrolyte layer in a sensed direction and, as a consequence, establish a reference oxygen partial pressure at the interface between the solid electrolyte layer and the reference electrode layer. (The particulars of this oxygen sensor will be described hereinafter.)

When disposed in an engine exhaust gas, this advanced oxygen sensor exhibits an output characteristic generally similar to that of the conventional oxygen sensor having a tubular solid electrolyte. Accordingly, this oxygen sensor is serviceable as a device to provide a feedback signal in an air/fuel ratio control system aiming at a stoichiometric air/fuel ratio. Moreover, this sensor has advantages such as unnecessity of using any reference gas, possibility of making small in size and good resistance to shocks and vibrations. However, the output characteristic of this oxygen sensor too is significantly affected by temperature. Particularly, when the temperature of the sensor is below about 500° C. the output characteristic changes such that it becomes difficult to make a comparison between a reference voltage of an adequate level and the output of the sensor. This is a matter of great inconvenience in practical air/fuel ratio control systems for automotive engines.

SUMMARY OF THE INVENTION

It is an object of the present invention to provide a device for producing a control signal for feedback control of the air/fuel ratio of an air-fuel mixture supplied to a combustor, such as combustion chambers of an internal combustion engine, which device includes an improved oxygen-sensitive element to be disposed in a combustion gas exhausted from the combustor and can produce an air/fuel ratio control signal according as an actual air/fuel ratio of the air-fuel mixture deviates from a stoichiometric air/fuel ratio with good stability and without being influenced by the temperature of the element even when the temperature is considerably low.

A device according to the invention comprises an oxygen-sensitive element which is to be disposed in a combustion gas exhausted from a combustor and comprises two oxygen concentration cells each constituted of a layer of an oxygen ion conductive solid electrolyte, a measurement electrode layer formed on one side of the solid electrolyte layer, a reference electrode layer formed on the other side of the solid electrolyte layer and a shield layer provided on the reference electrode side of the solid electrolyte layer so as to closely cover the reference electrode layer. At least one of the shield layer and the solid electrolyte layer has a microscopically porous and gas permeable structure, and one of the measurement electrode layer and the reference electrode layer of one concentration cell is electrically connected to the corresponding one of the measurement electrode layer and the reference electrode layer of the other cell. The device further comprises a constant voltage DC power source connected to the unconnected electrode layers of the respective concentration cells of the oxygen-sensitive element to force a DC current to flow through the solid electrolyte layers of the two cells, from the measurement electrode layer to the reference electrode layer in one cell and from the reference electrode layer to the measurement electrode layer in the other cell, and a signal-producing circuit having comparing means for making a comparison between a predetermined reference voltage and an output voltage of the oxygen-sensitive element developed between the measurement and reference electrode layers of predetermined one cell to examine which one of the reference voltage and the output voltage is higher than the other and signal-generating means for producing an air/fuel ratio control signal which varies according to a high-low relationship between the reference voltage and the output voltage examined by the comparing means.

The flow of the DC current in the two oxygen concentration cells causes migration of oxygen ions through the solid electrolyte layer of each cell in a direction reversely of the direction of the current flow. As a consequence, a reference oxygen partial pressure of a relatively high magnitude is maintained on the reference electrode side of one cell, whereas another oxygen partial pressure of a relatively low magnitude is maintained on the reference electrode side of the other cell. Therefore, in a combustion gas produced from a fuel-rich air-fuel mixture one of the two cells generates an electromotive force of a relatively high level while the other cell generates an electromotive force of a very low level, and in a combustion gas produced from a lean mixture containing excess air the levels of the electromotive forces of the two cells are reversed. Because of the flow of the same current in the two cells which are connected to each other in the manner as stated above, the aforementioned output voltage of the oxygen-sensitive element becomes independent of the electric resistance of the solid electrolyte layers in the element, so that the magnitude of this output voltage is scarcely influenced by the temperature of the element. The output voltage is at a constant level in a combustion gas produced from a rich mixture and at a differently constant level in a combustion gas produced from a lean mixture practically regardless of the temperature of the combustion gases. Accordingly, always it is possible to make a comparison between this output voltage and a fixed reference voltage corresponding to a stoichiometric air/fuel ratio, and, hence, the device according to the invention can produce a control signal for feedback control of the air/fuel ratio aiming at a stoichiometric air/fuel ratio with good stability and accuracy even when the combustion gas temperature is very low.

In principle, the two oxygen concentration cells in the oxygen-sensitive element may be mechanically separated from each other, but it is preferred to unite the two cells into a single element by uniting either the shield layers or the solid electrolyte layers of the two cells into a single layer which is made rigid and thick enough to serve as a structurally basic member or substrate of the entire element. Besides, the two measurement electrode layers or the two reference electrode layers which are electrically connected to each other may be united into a single electrode layer. The oxygen-sensitive element can be designed in a variety of forms as will be illustrated in the description of the preferred embodiments. In some cases, it is possible to utilize the solid electrolyte layer of each cell also as the shield layer for the reference electrode layer of the other cell.

For example, the signal-generating means in the present invention can be constituted of a combination of a voltage divider to which a constant source voltage is applied and a switching transistor the base of which is connected to the output terminal of the comparing means.

DETAILED DESCRIPTION OF THE INVENTION

Prior to a detailed description of preferred embodiments of the present invention, a conventionally popular oxygen sensor will be described briefly, and then an advanced oxygen sensor element according to U.S. patent application Ser. No. 12,763 will be described somewhat in detail.

Figure 1:
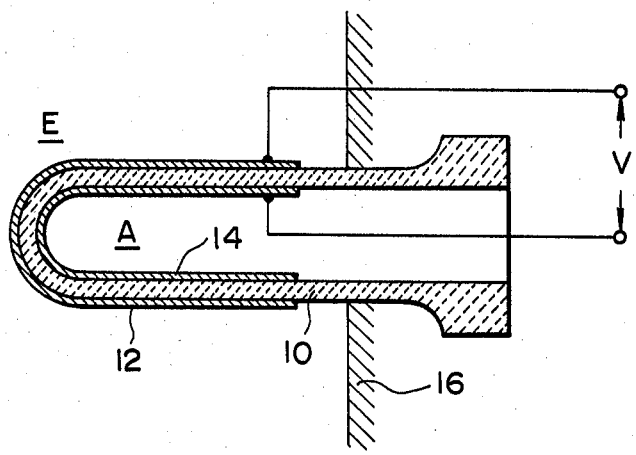
FIG. 1 is a schematic and sectional view of a conventional oxygen sensor.

FIG. 1 shows the construction of a conventional oxygen sensor currently used in automobile exhaust systems to detect the air/fuel ratio of air-fuel mixtures supplied to the engines. This oxygen sensor has a layer 10 of an oxygen ion conductive solid electrolyte, such as $ZrO_2$ stabilized with CaO or $Y_2O_3$, which is formed into the shape of a tube closed at one end. Formed on the outer side of the solid electrolyte type 10 is a thin and microscopically porous measurement electrode layer 12 which is exposed to an exhaust gas E when the sensor is attached to an exhaust pipe 16 for an automotive engine. Formed on the inner side of the solid electrolyte tube 10 is a thin and microscopically porous reference electrode layer 14 which is isolated from the exhaust gas and exposed to atmospheric air A utilized as the source of a reference oxygen partial pressure. Usually platinum is used as the material for the electrode layers 12 and 14.

Figure 2:
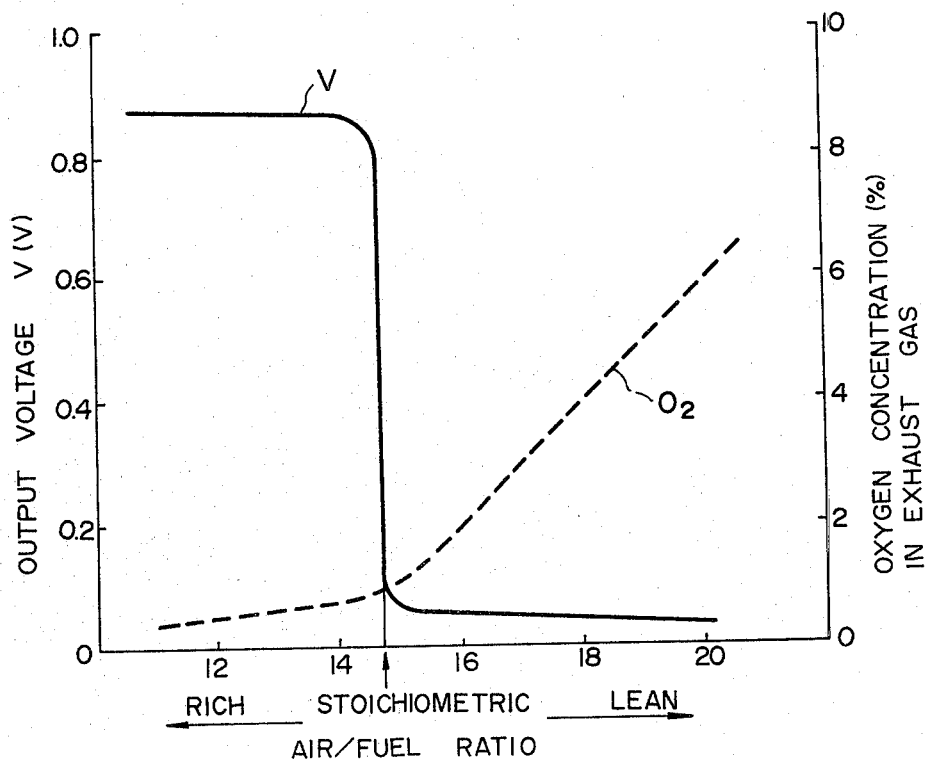
FIG. 2 is a graph showing dependence of oxygen concentration in an exhaust gas discharged from an engine and output voltage of the oxygen sensor of FIG. 1 disposed in the exhaust gas on the air/fuel ratio of an air-fuel mixture supplied to the engine.

The concentration of oxygen in the exhaust gas E depends primarily on the air/fuel ratio of an air-fuel mixture subjected to combustion in the engine and, as represented by curve $O_2$ in FIG. 2, gradually increases as the air/fuel ratio becomes higher. However, an electro-motive force generated across the solid electrolyte layer 10 as output voltage V of the oxygen sensor of FIG. 1 in the exhaust gas is not proportional to the oxygen concentration in the exhaust gas. While a fuel-rich mixture is supplied to the engine, a local oxygen concentration at the surface of the measurement electrode layer 12 becomes almost zero because there occur oxidation reactions of CO, HC (unburned hydrocarbons), etc. contained in the exhaust gas at the surface of the electrode layer 12 which is made of a catalytic material such as platinum, so that a great difference in oxygen partial pressure is produced between the outer and inner sides of the solid electrolyte layer 10. Therefore, the output voltage V of the oxygen sensor remains practically constantly at a maximally high level so long as the air/fuel ratio is below a stoichiometric ratio (about 14.7 for air-gasoline mxiture) as represented by curve V in FIG. 2. While a lean mixture is supplied to the engine, a difference in oxygen partial pressure between air A and the exhaust gas E becomes very small, so that the output voltage V of the sensor remains practically constantly at a minimally low level. Therefore, the output voltage of this oxygen sensor in the exhaust gas E exhibits a great and abrupt change as can be seen in FIG. 2 when the air/fuel ratio changes across the stoichiometric ratio. In other words, in the exhaust gas E this oxygen sensor exhibits an on-off type output characteristic with respect to the air/fuel ratio. The output voltage V of this oxygen sensor is affected by the temperature of the sensor, and the characteristic curve V in FIG. 2 represents experimental data obtained at a constant temperature of 600° C.

In conventional air/fuel ratio control systems which utilize an oxygen sensor of the type as shown in FIG. 1 to maintain a stoichiometric air/fuel ratio, the output voltage of the oxygen sensor is used as a feedback signal and compared with a fixed reference voltage which corresponds to the stoichiometric air/fuel ratio (for example, 500 mV in the case of the sensor output characteristic of FIG. 2). While the output voltage is higher than the reference voltage a judgement that a fuel-rich mixture is being supplied to the engine is made, and accordingly a control signal to decrease the fuel feed rate is produced. While the output voltage of the sensor is below the reference voltage a judgement that a lean mixture (containing excess air) is being supplied to the engine, and produced is a control signal to increase the fuel feed rate. In practice, however, this oxygen sensor has disadvantages in several respects as mentioned hereinbefore.

Figure 3:
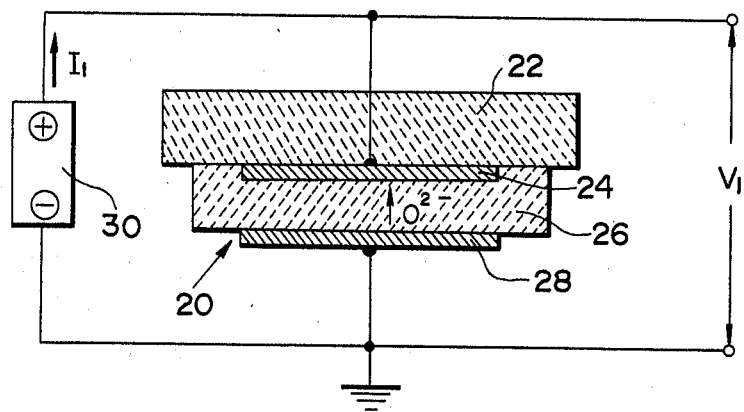
FIGS. 3 and 4 show schematically and sectionally a fundamental construction of a recently developed oxygen-sensitive element for the explanation of the principle of the function of the element.

FIG. 3 shows a fundamental construction of an advanced oxygen-sensitive element 20 disclosed in U.S. patent application Ser. No. 12,763 and an air/fuel ratio detecting device using the same element. This oxygen-sensitive element 20 has a shield layer 22 which is made of an electrochemically inactive and heat-resistant material and thick enough to serve as a structurally basic member or substrate of the element 20. A reference electrode layer 24, an oxygen ion conductive solid electrolyte layer 26 and a measurement electrode layer 28 are formed on the shield layer 22 one upon another such that the reference electrode layer 24 is sandwiched between the shield layer 22 and the solid electrolyte layer 26 and, macroscopically, entirely shielded from the environmental atmosphere. The measurement electrode layer 28 on the outer side of the solid electrolyte layer 26 is made to have a microscopically porous and gas permeable structure, and at least one of the solid electrolyte layer 26 and the shield layer 22, usually the former, is made to have a microscopically porous and gas permeable structure. It will be understood that the solid electrolyte layer 26 and the two electrode layers 24, 28 constitute an oxygen concentration cell which generates an electromotive force when there is a difference in oxygen partial pressure between the reference electrode side and the measurement electrode side of the solid electrolyte layer 26. In this element 20, it is not intended to introduce a certain reference gas to the surface of the reference electrode laye 24. Instead, a DC power supply 30 is connected to the reference and measurement electrode layers 24 and 28 to force a DC current to flow through the solid electrolyte layer 26 between the two electrode layers 24 and 28 in a selected direction.

In the case of FIG. 3, the DC power supply 30 is connected to the reference and measurement electrode layers 24 and 28 such that a current $I_1$ flows through the solid electrolyte layer 26 from the reference electrode layer 24 towards the measurement electrode layer 28. When, therefore, this element 20 is disposed in an oxygen-containing gas there occurs ionization of oxygen molecules at the measurement electrode layer 28, and the formed oxygen ions migrate through the solid electrolyte layer 26 towards the reference electrode layer 24. The oxygen ions arrived at the reference electrode layer 24 are converted to oxygen molecules, so that there is a tendency that oxygen accumulates on the reference electrode side of the solid electrolyte layer 26 with a resultant rise in oxygen partial pressure on this side. However, the accumulated oxygen continues to flow out through the porous solid electrolyte layer 26. Therefore, a nearly constant oxygen partial pressure is established at the interface between the reference electrode layer 24 and the solid electrolyte layer 26 after the lapse of a short period of time. Then the concentration cell in the element 20 generates an electromotive force indicative of an oxygen partial pressure at the measurement electrode layer 28 relative to the nearly constant oxygen pressure established at the reference electrode layer 24. An output voltage $V_1$ attributed to this electromotive force can be measured between the reference and measurement electrode layers 24 and 28.

Figure 5:
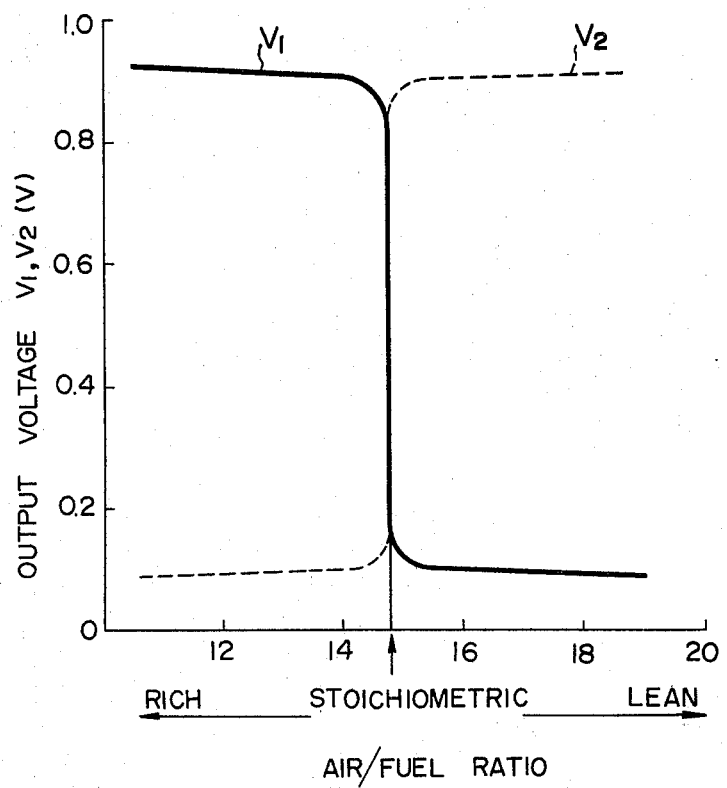
FIG. 5 is a graph showing output characteristics of the oxygen-sensitive element of FIGS. 3 and 4 in an engine exhaust gas.

When this element 20 is disposed in an exhaust gas of an internal combustion engine with the supply of a DC current of an appropriate intensity in the way as shown in FIG. 3, the output voltage $V_1$ becomes either considerably high or very low according as the engine is fed with a rich mixture or a lean mixture. While a rich mixture is fed to the engine, the supply of oxygen to the reference electrode layer 24 by migration of oxygen ions thereto produces a considerable effect compared with littleness of inward diffusion of gaseous oxygen contained in the exhaust gas through the porous solid electrolyte layer 24. The magnitude of a constant reference oxygen partial pressure established on the reference electrode side depends on various factors such as the exhaust gas temperature, intensity of the DC current $I_1$ and the thickness and structure of the solid electrolyte layer 24. By way of example, a reference oxygen partial pressure of $10^0$–$10^2$ atm is established when the exhaust gas temperature is 600° C. and the current intensity is 3 μA, whereas the oxygen partial pressure in the exhaust gas is $10^{-2}$–$10^{-3}$ atm. Accordingly, while a rich mixture is fed to the engine the output voltage $V_1$ remains at a considerably high level as represented by curve $V_1$ (solid line) in FIG. 5. However, when a lean mixture is fed to the engine the effect of the migration of oxygen ions to the reference electrode 24 becomes relatively small compared with inward diffusion of an increased quantity of gaseous oxygen through the solid electrolyte layer 26. As a consequence the difference between the reference oxygen partial pressure on the reference electrode side and the oxygen partial pressure in the exhaust gas becomes very small, so that the output voltage $V_1$ remains at a very low level as shown in FIG. 5. Accordingly, a great and sharp change occurs in the level of the output voltage $V_1$ when the air/fuel ratio of a mixture supplied to the engine changes across the stoichiometric ratio. Therefore, the device of FIG. 3 can serve the same function as the conventional oxygen sensor of FIG. 1 in a combustion gas.

Figure 4:
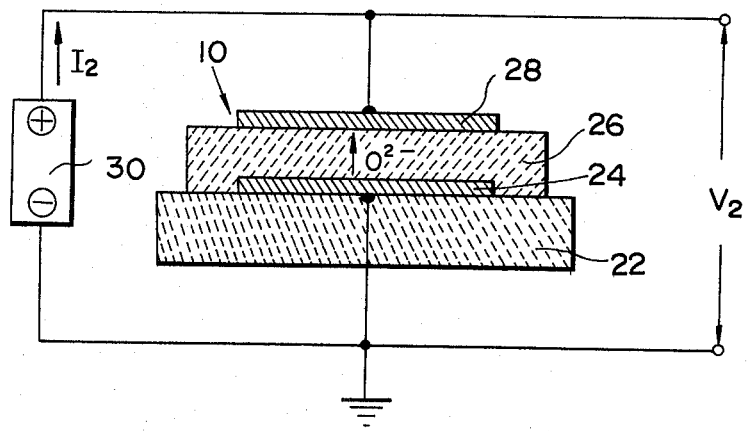

FIG. 4 shows another case where the DC power supply 30 is connected to the reference and measurement electrode layers 24 and 28 of the oxygen-sensitive element 20 such that a DC current $I_2$ flows through the solid electrolyte layer 26 from the measurement electrode layer 28 towards the reference electrode layer 24. In this case, oxygen molecules diffused to the reference electrode layer 24 are ionized at this electrode layer 24, and the formed oxygen ions migrate outwardly through the solid electrolyte layer 26. At the measurement electrode layer 28, the oxygen ions converted to gaseous oxygen which is liberated into the exterior gas atmosphere. Therefore, there is a tendency of lowering of an oxygen partial pressure on the reference electrode side of the solid electrolyte layer 26. Balanced by inward diffusion of oxygen molecules through the solid electrolyte layer, soon a nearly constant and relatively low oxygen partial pressure is established at the interface between the reference electrode layer 24 and the solid electrolyte layer 26. In an exhaust gas discharged from an internal combustion engine operated with a lean mixture, the magnitude of the thus established reference oxygen partial pressure becomes $10^{-20}$–$10^{-22}$ atm, for example, when the exhaust gas temperature is 600° C. and the intensity of the DC current $I_2$ is 3 μA. Accordingly output voltage $V_2$ of the element 20 in this case remains at a considerably high level as represented by curve $V_2$ (broken line) in FIG. 5. When a rich mixture is supplied to the engine, the output voltage $V_2$ remains at a very low level as shown in FIG. 5 because ionization of oxygen at the reference electrode layer 24 becomes insignificant by reason of a great decrease in the quantity of gaseous oxygen inwardly diffusing through the solid electrolyte layer 26. Therefore, also in this case a great and sharp change occurs in the level of the output voltage $V_2$ when the air/fuel ratio of a mixture supplied to the engine changes across the stoichiometric ratio.

Either in the case of FIG. 3 or in the case of FIG. 4, it is desirable that the DC power supply 30 is of a constant current type so that the current $I_1$ or $I_2$ forced to flow through the solid electrolyte layer 26 between the two electrode layers 24 and 28 is a constant current.

Figure 7:
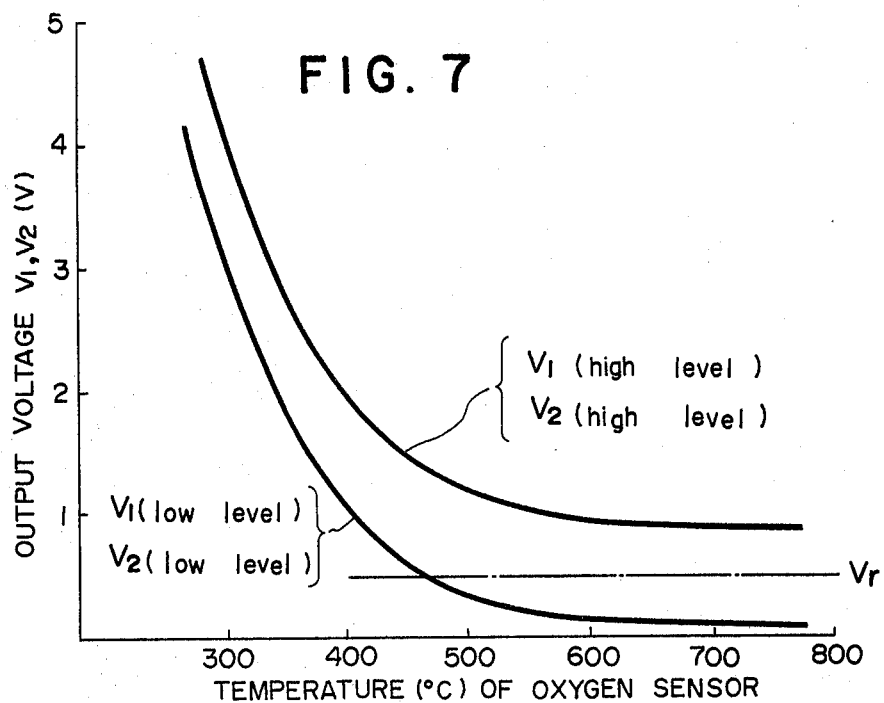
FIGS. 7 and 8 are graphs showing the dependence of the output voltage of the oxygen-sensitive element of FIGS. 3 and 4 in an engine exhaust gas on the temperature of the element.
Figure 8:
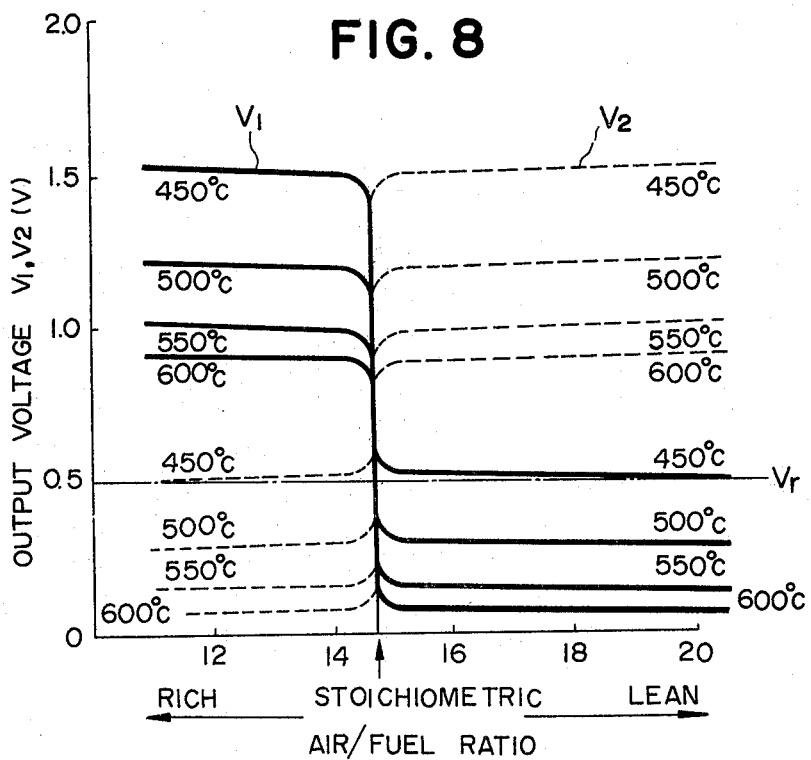

In the device of either FIG. 3 or FIG. 4, the DC power supply 30 and a voltage measuring instrument (not shown) are both connected between the reference and measurement electrode layers 24 and 28. Accordingly the output voltage $V_1$ or $V_2$ of the oxygen-sensitive element 20 becomes the sum of an electromotive force the element 20 generates and a voltage developed across the solid electrolyte layer 26, which has an electrical resistance R, by the flow of the constant current $I_1$ or $I_2$ therethrough, that is, a voltage expressed by $I_1 \times R$ or $I_2 \times R$. The resistance R of the solid electrolyte layer 26 depends significantly on the temperature of the element 20 as shown exemplarily in FIG. 6: the resistance R greatly increases as the temperature of the element 20 lowers. Therefore, the output voltage $V_1$ or $V_2$ is significantly affected by the temperature of the element 20. As shown in FIGS. 7 and 8, there is a tendency that the output voltage $V_1$ or $V_2$ becomes higher as the temperature lowers, and this tendency becomes very strong when the temperature is below a certain level, for example below about 550° C.

In performing feedback control of air/fuel ratio in an internal combustion engine by using the device of FIG. 3 or FIG. 4, it will be natural to compare the output voltage $V_1$ or $V_2$ with a fixed reference voltage $V_r$ of 0.5 V if a normal output characteristic of the device of FIG. 3 or 4 is as shown in FIG. 5. FIGS. 7 and 8 show that if the temperature of the oxygen-sensitive element 20 is below 450° C. the output voltage $V_1$ or $V_2$ remains above the reference voltage $V_r$ whether a rich mixture or a lean mixture is supplied to the engine, meaning that the feedback control of air/fuel ratio becomes impossible. In other words, stable operation of a feedback air/fuel ratio control system including the device of FIG. 3 or 4 is difficult while the temperature of the element 20 or exhaust gas temperature is below, for example, about 550° C.

As mentioned hereinbefore, the present invention solves this problem and enables to make the best use of the essential features of the advanced oxygen-sensitive element.

Figure 9:
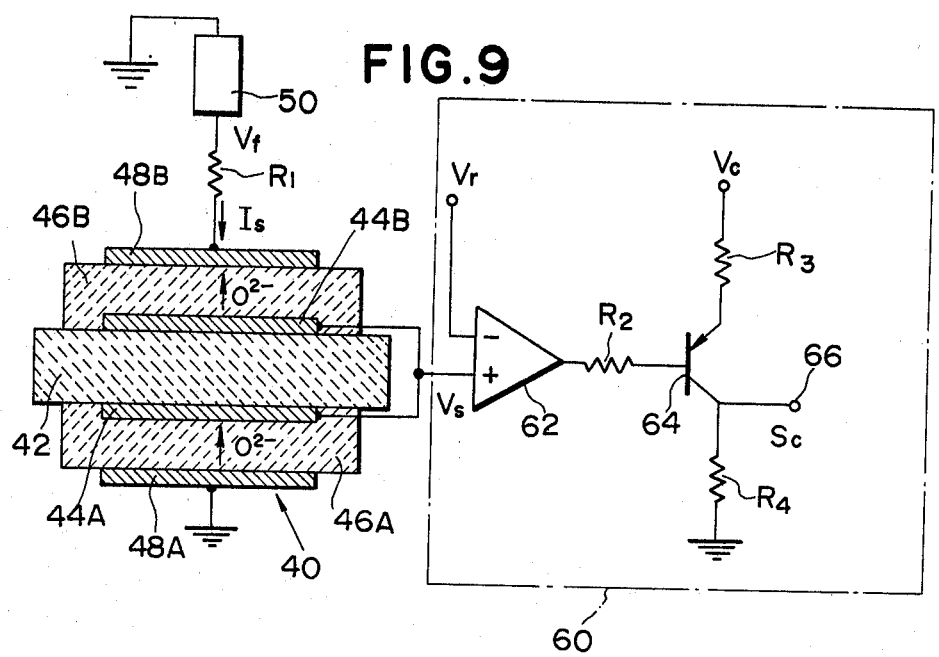
FIG. 9 is a schematic and partly sectional illustration of a control signal producing device as an embodiment of the present invention.

FIG. 9 shows an air/fuel ratio control signal producing device as an embodiment of the present invention. Essentially this device is constituted of an oxygen-sensitive element 40, a constant voltage DC power source 50, and a signal-producing circuit 60.

The oxygen-sensitive element 40 has a shield layer 42 which is rigid and thick enough to serve as a substrate of this element 40. On one side of the shield layer 42, a first reference electrode layer 44A, a first oxygen ion conductive solid electrolyte layer 46A and a first measurement electrode layer 48A are formed one upon another such that macroscopically the reference electrode layer 44A is entirely shielded from the environmental atmosphere by the shield layer 42 and the solid electrolyte layer 46A. Each of the three layers 44A, 46A and 48A is a thin film-like layer, and the measurement electrode layer 48A and the solid electrolyte layer 46A are both microscopically porous and gas permeable. On the opposite side of the shield layer 42, a second reference electrode layer 44B, a second oxygen conductive solid electrolyte layer 46B and a second measurement electrode layer 48B are formed one upon another generally symmetrically with the corresponding layers 44A, 46A and 48A on the other side. Macroscopically the second reference electrode layer 44B is entirely shielded from the environmental atmosphere, and the second measurement electrode layer 48B and second solid electrolyte layer 46B are microscopically porous and gas permeable.

Thus, this element 40 can be regarded as a combination of two sets of oxygen concentration cells: that is, one constituted of the first solid electrolyte layer 46A, the first reference and measurement electrode layers 44A, 48A and the shield layer 42; and the other constituted of the second solid electrolyte layer 46B, the second reference and measurement electrode layers 44B, 48B and the shield layer 42 which is utilized by the two cells in common.

The first reference electrode layer 44A and the second reference electrode layer 44B are electrically connected to each other as illustrated, and the constant voltage DC power source 50 is connected to the second and first measurement electrode layers 48B and 48A of the oxygen-sensitive element 40 via a resistance $R_1$ so as to apply a constant voltage $V_f$ to the element 40 thereby to force a current $I_s$ to flow through the second and first solid electrolyte layers 46B and 46A. In the illustrated case the second measurement electrode layer 48B is connected to the positive terminal of the power source 50, so that in the second concentration cell the current $I_s$ flows from the measurement electrode 48B to the reference electrode 44B and in the first cell from the reference electrode 44A to the measurement electrode 48A. Accordingly, when the oxygen-sensitive element 40 is disposed in an oxygen-containing gas such as an engine exhaust gas there occurs ionization of oxygen at the first measurement electrode layer 48A, and the formed oxygen ions migrate through the first solid electrolyte layer 46A towards the first reference electrode layer 44A, whereas in the second cell on the opposite side oxygen ions migrate through the second solid electrolyte layer 46B from the reference electrode layer 44B towards the measurement electrode layer 48B. Therefore, when the element 40 is disposed in an exhaust gas of a gasoline engine the first cell (on the lower side in FIG. 9) exhibits an output characteristic as represented by curve $V_1$ in FIG. 5, while the second cell (on the upper side) exhibits an output characteristic as represented by curve $V_2$ in FIG. 5. As a combination of such two oxygen concentration cells with their reference electrode layers 44A and 44B connected to each other, the element 40 of FIG. 9 provides an output voltage $V_s$ developed between the reference and measurement electrode layers 44A and 48A of the first cell. The nature of this output voltage $V_s$ will be described with reference to FIG. 10, wherein the element 40 of FIG. 9 is illustrated in the form of an equivalent circuit.

Figure 10:
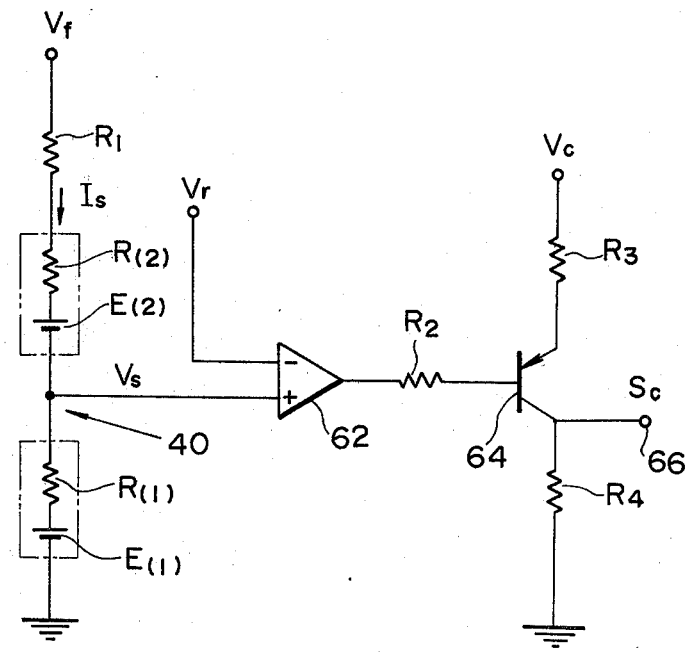
FIG. 10 is an equivalent circuit diagram for the device of FIG. 9.

In FIG. 10, the first oxygen concentration cell of the element 40 is expressed as a cell having an internal resistance $R_{(1)}$ principally attributed to the first solid electrolyte layer 46A and generating an electromotive force $E_{(1)}$. Similarly, the second cell has an internal resistance $R_{(2)}$ principally attributed to the second solid electrolyte layer 46B and generates an electromotive force $E_{(2)}$. Since the two cells are connected in series, the application of the constant voltage $V_f$ to the element 40 causes a current $I_s$ to flow in both cells with the same current intensity. This current $I_s$ is expressed by:

$$I_s = \frac{V_f - (E_{(1)} + E_{(2)})}{R_{(1)} + R_{(2)}} \tag{1}$$

(The resistance $R_1$ is neglected since the existence of this resistance $R_1$ is nonessential in considering the principle of the element 40.)

When the exhaust gas is the product of combustion of either a rich mixture or a lean mixture, the levels of the electromotive forces $E_{(1)}$ and $E_{(2)}$ generated by the respective cells become roughly as follows, though these values are affected by the temperature of the element 40.

| Mixture supplied to Engine | Rich Mixture | Lean Mixture |
|---|---|---|
| EMF of first Cell, $E_{(1)}$ | 1.0 (V) | 0.1 (V) |
| EMF of Second Cell, $E_{(2)}$ | 0.1 (V) | 1.0 (V) |
| $E_{(1)} + E_{(2)}$ | 1.1 (V) | 1.1 (V) |

Thus, the sum of $E_{(1)}$ and $E_{(2)}$ does not vary whether a rich mixture or a lean mixture is supplied to the engine, so that the intensity of the current $I_s$ given by Equation (1) is constant so long as the element 40 remains at a constant temperature. Owing to this fact, the oxygen-sensitive element 40 has an advantage that reference oxygen pressures established at the respective reference electrode layers 44A and 44B are scarcely influenced by changes in the composition of the exhaust gas resulting from changes in the air/fuel mixing ratio of a mixture supplied to the engine.

The internal resistances $R_{(1)}$ and $R_{(2)}$ of the element 40 undergo changes as the temperature of the element 40 varies, but always there holds a relationship $R_{(1)} = R_{(2)} = R_{(s)}$ even if the temperature of the element 40 changes during operation because the two cells in this element 40 are constructed substantially identically. Therefore, Equation (1) can be rewritten into:

$$I_s = \frac{V_f - (E_{(1)} + E_{(2)})}{2R_{(s)}} \tag{2}$$

Figure 6:
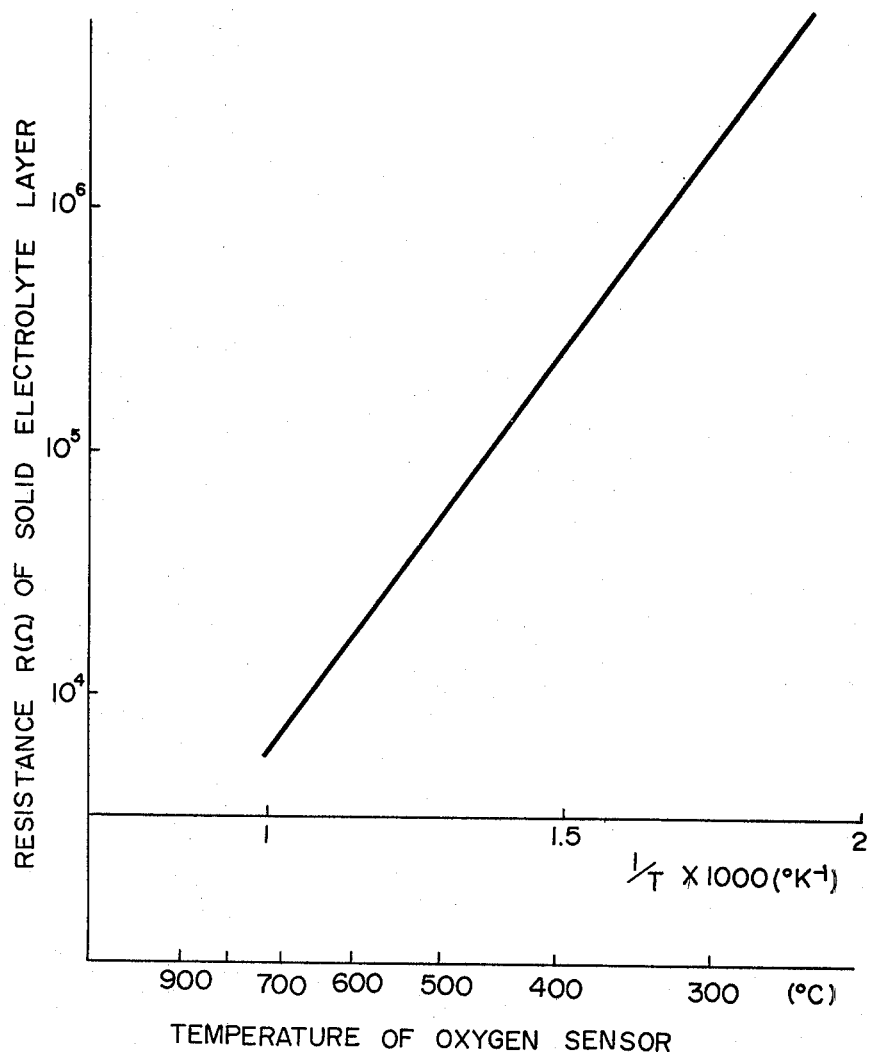
FIG. 6 is a graph showing the dependence of the electrical resistance of a solid electrolyte layer in the oxygen-sensitive element of FIGS. 3 and 4 on temperature.
Figure 11:
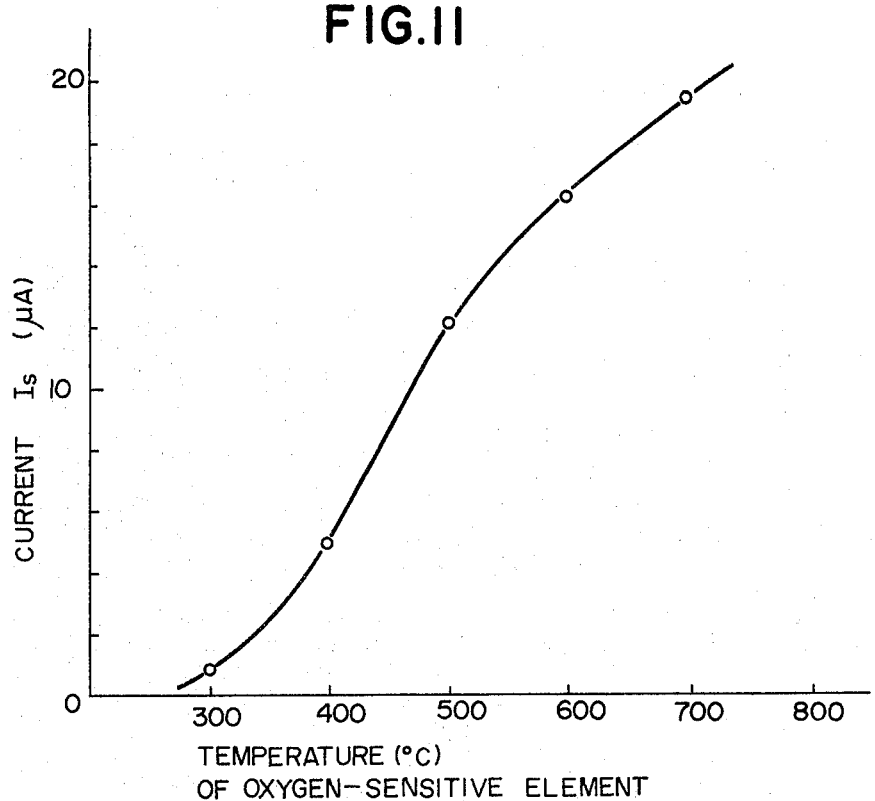
FIG. 11 is a graph showing the dependence of a current flowing in the oxygen-sensitive element of the device of FIG. 9 on the temperature of the element.

Because of the internal resistance $R_{(s)}$ of each cell in the element 40 having a temperature dependence as represented by the curve of FIG. 6, the intensity of the current $I_s$ given by Equation (2) varies as the temperature of the element 40 varies. More particularly, the current $I_s$ becomes smaller while the temperature of the element 40 is relatively low so that only a relatively small quantity of gas diffuses through each solid electrolyte layer 46A, 46B, but becomes larger as the temperature of the element 40 rises so that an increased quantity of gas diffuses through each solid electrolyte layer 46A, 46B. For example, FIG. 11 shows the relationship between the temperature of the element 40 and the intensity of the current $I_s$ flowing in the element 40 observed when the magnitude of the constant voltage $V_f$ was 0.5 volts.

As will be understood from the diagram of FIG. 10, the output voltage $V_s$ of the oxygen-sensitive element 40 can be expressed by:

$$V_s = E_{(1)} + I_s \cdot R_{(1)} = E_{(1)} + I_s \cdot R_{(s)} \qquad (3)$$

By combining Equation (2) with Equation (3), $$\begin{aligned} V_s &= E_{(1)} - R_{(s)} \frac{V_f + (E_{(1)} + E_{(2)})}{2R_{(s)}} \\ &= E_{(1)} + \frac{V_f - (E_{(1)} + E_{(2)})}{2} \\ &= \frac{V_f}{2} + \frac{E_{(1)} - E_{(2)}}{2} \end{aligned} \qquad (4)$$

Equation (4) shows that the output voltage $V_s$ is independent of the resistance $R_{(s)}$ of each oxygen concentration cell. Therefore, the output voltage $V_s$ of the element 40 of FIG. 9 is not affected by considerable changes in the magnitude of a voltage given by $I_s \times R_{(s)}$ with changes in the temperature of the element 40 as hereinbefore explained with reference to FIGS. 7 and 8. That is, the output voltage $V_s$ is scarcely influenced by the temperature of the element 40, aside from slight dependence of the electromotive forces $E_{(1)}$ and $E_{(2)}$ on temperature, and varies almost solely according to changes in the composition of the exhaust gas resulting from changes between a rich mixture and a lean mixture supplied to the engine. Because of such a nature, the output voltage $V_s$ of the oxygen-sensitive element 40 serves as an ideal feedback signal for feedback control of air/fuel ratio.

The control signal producing circuit 60 has a comparator 62 and a switching transistor 64. The first and second reference electrode layers 44A and 44B, which are connected to each other, of the element 40 is connected to the positive input terminal of the comparator 62, so that the output voltage $V_s$ of the element 40 is applied to the positive input terminal of the comparator 62, and a constant voltage $V_r$ is applied to the negative input terminal of the comparator 62 as a reference voltage. The output terminal of the comparator 62 is connected to the base of the switching transistor 64 via a resistance $R_2$. A source of a constant voltage $V_c$ is connected to the collector of the transistor 64 through a resistance $R_3$, and the emitter of the transistor 64 is grounded through a resistance $R_4$. When the transistor 64 is conducting, the resistances $R_3$ and $R_4$ constitute a voltage divider. Connected to an output terminal on the emitter side of this voltage divider is an output terminal 66 of the circuit 60.

When the oxygen-sensitive element 40 is electrically connected as illustrated in FIG. 9 and disposed in an exhaust gas of an internal combustion engine, the output voltage $V_s$ becomes relatively high while a rich mixture is supplied to the engine and relatively low in the case of a lean mixture. The reference voltage $V_r$ is set at a value between the high and low levels of the output voltage $V_s$. If a rich mixture is supplied to the engine, the output voltage $V_s$ taken as a feedback signal becomes higher than the reference voltage $V_r$, meaning that the comparator 62 receives a greater input at its positive input terminal than at the negative input terminal. Accordingly the comparator 62 provides an output voltage to the base of the switching transistor 64, so that the transistor 64 becomes conducting and allows the source voltage $V_c$ to provide a control signal $S_c$ of a predetermined voltage at the output terminal 66 of the signal-producing circuit 60. For example, when the source voltage $V_c$ is 12 V, resistance $R_3$ is 11 KΩ and resistance $R_4$ is 1 KΩ, the amplitude of the control signal $S_c$ becomes 1 V. This control signal $S_c$ is supplied to a fuel feed regulating means (not shown) to decrease the fuel feed rate until the stoichiometric air/fuel ratio is realized. If a lean mixture is supplied to the engine the output voltage $V_s$ becomes lower than the reference voltage $V_r$, meaning that the comparator 62 receives a greater input at its negative input terminal than at the positive input terminal. Accordingly the comparator 62 stops producing an output, so that the transistor 64 becomes nonconducting. Therefore, the control signal $S_c$ at the output terminal 66 becomes a zero volt signal, which causes the fuel feed regulating means to increase the fuel feed rate until realization of the stoichiometric air/fuel ratio.

Figure 12:
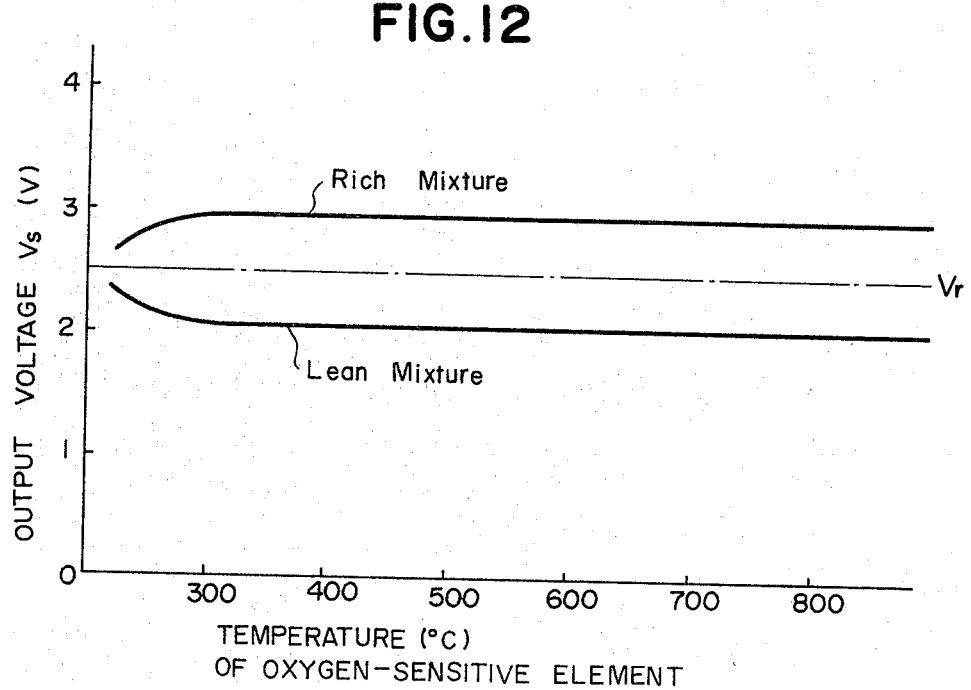
FIG. 12 is a graph showing the dependence of the output characteristics of the oxygen-sensitive element of the device of FIG. 9 in exhaust gases on the temperature of the element.

FIG. 12 shows an example of output characteristics of the oxygen-sensitive element 40 of FIG. 9 in exhaust gases of an internal combustion engine. The constant voltage $V_f$ applied to the element 40 was 5.0 V, and the current $I_s$ flowed in the direction as illustrated in FIG. 9. The magnitude of the output voltage $V_s$ became about 3 V while a rich mixture was supplied to the engine because the electromotive force $E_{(1)}$ generated by the first cell in this element 40 under this condition was about 1.0 V, while the electromotive force $E_{(2)}$ generated by the second cell was about 0.1 V. (According to Equation (4), $V_s$ in this case becomes 2.5 V + about 0.45 V.) When a lean mixture was supplied to the engine, the magnitude of the output voltage $V_s$ lowered to about 2 V as will be understood from Equation (4) and the foregoing numerical values of high and low levels of $E_{(1)}$ and $E_{(2)}$. As can can be seen in FIG. 12, the high and low values of the output voltage $V_s$ were not affected by the temperature of the element 40, i.e. the temperature of the exhaust gases, except when the exhaust gas temperature was extremely low. In the signal-producing device comprising the oxygen-sensitive element 40 exhibiting the output characteristics of FIG. 12, it is suitable to set the reference voltage $V_r$ at the level of about 2.5 V.

Figure 13:
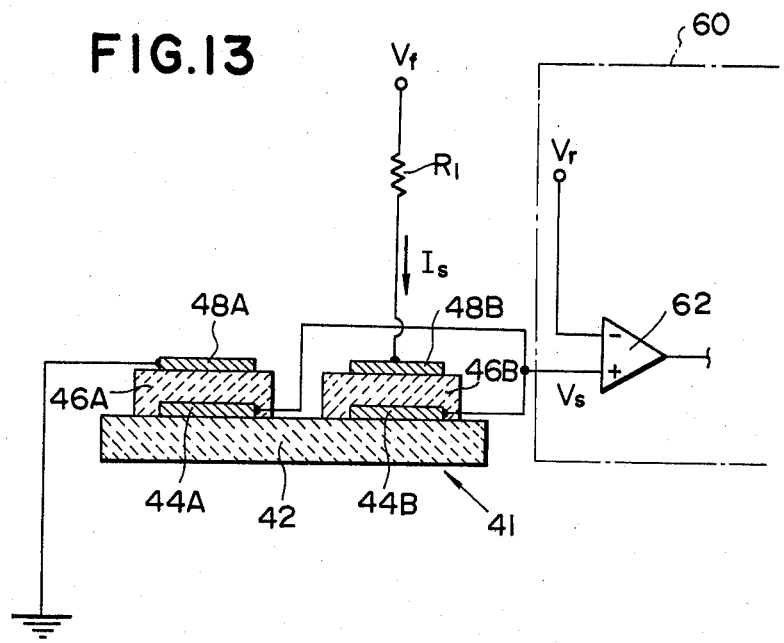
FIGS. 13–19 show, each in a view similar to FIG. 9, seven differently designed devices embodying the present invention, respectively.

FIG. 13 shows another embodiment of the present invention. An oxygen-sensitive element 41 in this signal-producing device is similar in principle to the element 40 in FIG. 9 but different in the arrangement of the two oxygen concentration cells. The combination of the first reference electrode layer 44A, first solid electrolyte layer 46A and first measurement electrtode layer 48A is formed so as to occupy a limited portion of the surface area of the shield layer 42. Spaced from this combination, but on the same side of the shield layer 42, the combination of the second reference electrode layer 44B, second solid electrolyte layer 46B and second measurement electrode layer 48B is formed similarly to the first combination of the three layers 44A, 46A, 48A. The shield layer 42 is common to the two concentration cells and serves also as the substrate of the entire element 41. In other respects, the device of FIG. 13 is identical with the device of FIG. 9. The first and second reference electrode layers 44A and 44B are connected to each other, and the constant voltage DC power source 50 is connected to the measurement electrode layers 48A and 48B. The positive input terminal of the comparator 62 is connected to the reference electrode layers 44A, 44B to receive the output voltage $V_s$ of the element 41. Therefore, the function of the signal-producing device of FIG. 13 with the element 41 disposed in a combustion gas is identical with the function of the device of FIG. 9.

Figure 14:
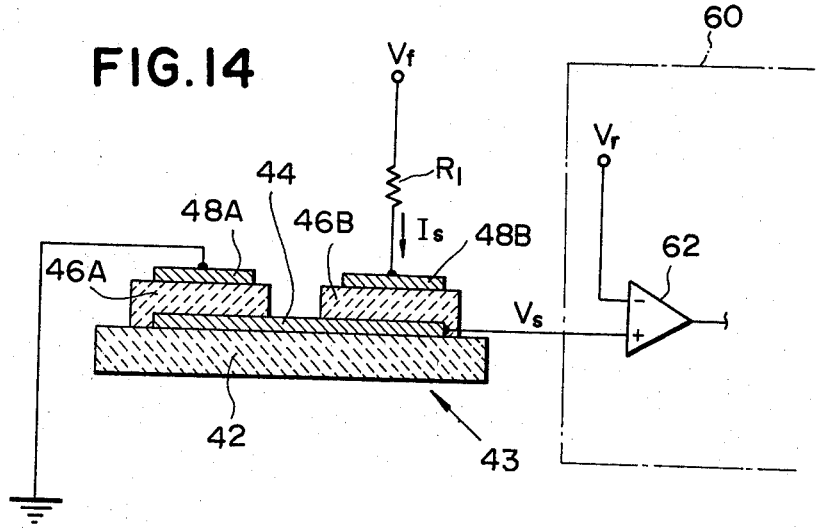

FIG. 14 shows a modification of the oxygen-sensitive element 41 of FIG. 13. An oxygen-sensitive element 43 of FIG. 14 differs from the element 41 of FIG. 13 only in that this element 43 has a single reference electrode layer 44 which is common to the two oxygen concentration cells and can be regarded as the union of the first and second reference electrode layers 44A and 44B in FIG. 13. This single reference electrode layer 44 is connected to the positive input terminal of the comparator 62. It will be understood that the device of FIG. 14 functions identically to the device of FIG. 13. In this case the shield layer 42 may be made of an electrically conducting material, and, moreover, it is possible to integrate the shield layer 42 and the reference electrode layer 44 into a single member.

Figure 15:
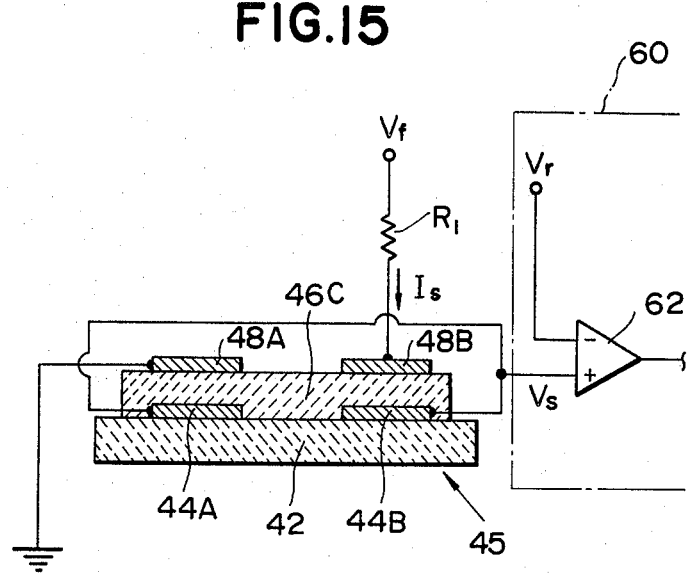

FIG. 15 shows an oxygen-sensitive element 45 which is fundamentally similar to the element 41 of FIG. 13. As a sole modification, this element 45 has a single solid electrolyte layer 46C which can be regarded as the union of the first and second solid electrolyte layers 46A and 46B in FIG. 13. That is, a part of this solid electrolyte layer 46C intervening between the first reference and measurement electrode layers 44A and 48A is utilized as an essential constituent of the first oxygen concentration cell and another part intervening between the second reference and measurement electrode layers 44B and 48B as a constituent of the second cell. As will be understood, this modification does not affect the function of the oxygen-sensitive element.

Figure 16:
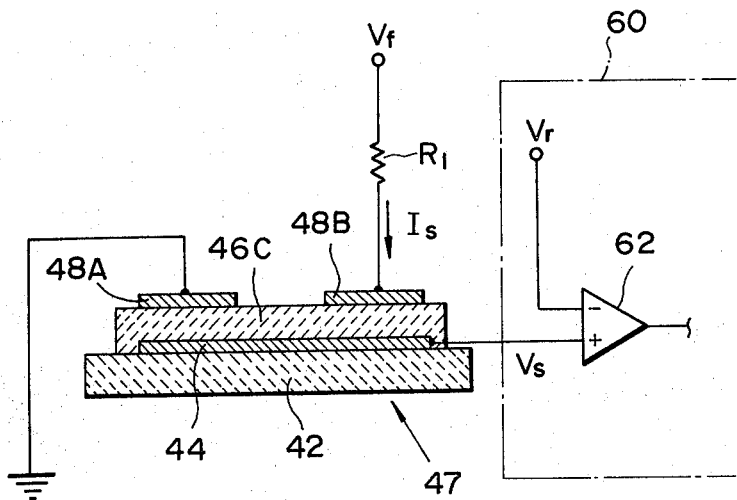

FIG. 16 shows a further modification of the element 45 of FIG. 15. In place of the two reference electrode layers 44A and 44B in FIG. 15, an oxygen-sensitive element 47 of FIG. 16 has a single reference electrode layer 44 which is common to the two oxygen concentration cells. Similarly to the element 43 of FIG. 14, the shield layer 42 in FIG. 16 may be made of an electrically conducting material and, if desired, may be integrated with the single reference electrode layer 44.

Figure 17:
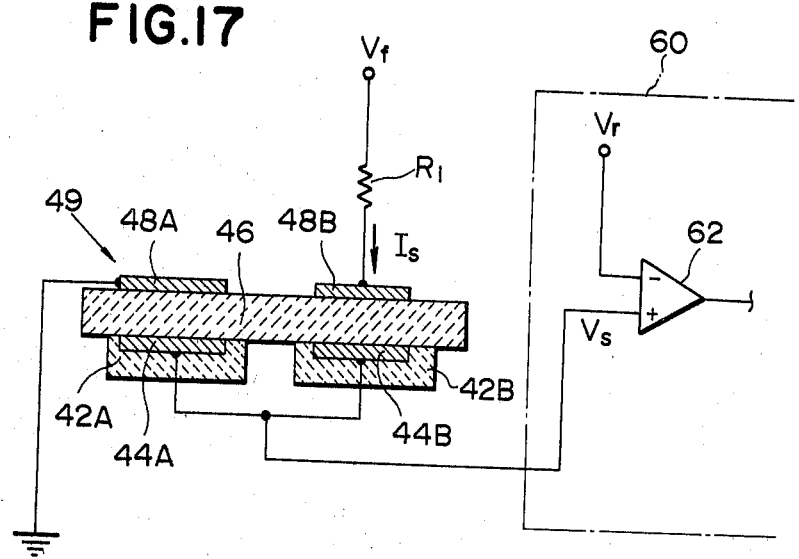

FIG. 17 shows another modification of the oxygen-sensitive element 41 of FIG. 13. An element 49 of FIG. 17 has a single solid electrolyte layer 46 which is in the form of a rigid plate thick enough to serve as a structurally basic member or substrate of the element 49. On one side of this solid electrolyte layer 46, a thin first reference electrode layer 44A and a similar second reference electrode layer 44B are formed with a distance therebetween. On the same side of the solid electrolyte layer 46, a first shield layer 42A is formed so as to closely cover the first reference electrode layer 44A and a second shield layer 42B to closely cover the second reference electrode layer 44B. On the opposite side of the solid electtrolyte layer 46, first measurement electrode layer 48A is formed so as to occupy a limited area and lie generally opposite to the first reference electrode layer 44A, and on the same side second measurement electrode layer 48B is formed so as to be spaced from the first measurement electrode layer 48A and lie generally opposite to the second reference electrode layer 44B. The two reference electrode layers 44A and 44B are connected to each other and to the positive input terminal of the comparator 62, and the constant voltage $V_f$ is applied to the element 49 in the same way as in the foregoing embodiments. Accordingly this oxygen-sensitive element 49 does not differ in function from the element 41 of FIG. 13.

Also in this case, the solid electrolyte layer 46 may be made microscopically porous and gas permeable. Alternatively, this solid electrolyte layer 46 may be made to have a tight, dense and practically gas impermeable structure, conditioning that then the first and second shield layers 42A and 42B are made microscopically porous and gas permeable. When the solid electrolyte layer 46 is gas impermeable but the shield layers 42A, 42B are gas permeable, the reference electrode layers 44A, 44B are also made gas permeable.

Figure 18:
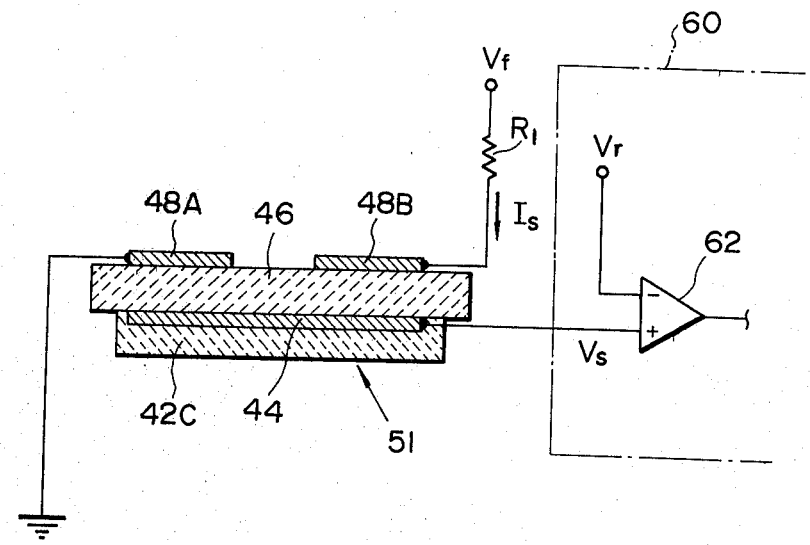

An oxygen-sensitive element 51 shown in FIG. 18 is a modification of the element 49 of FIG. 17 and has a single reference electrode layer 44 which is covered with a single shield layer 42C and opposed to both the first and second measurement electrode layers 48A and 48B. This reference electrode layer 44 is connected to the positive input terminal of the comparator 62, so that the element 51 does not differ in function from the element 49 of FIG. 17.

Figure 19:
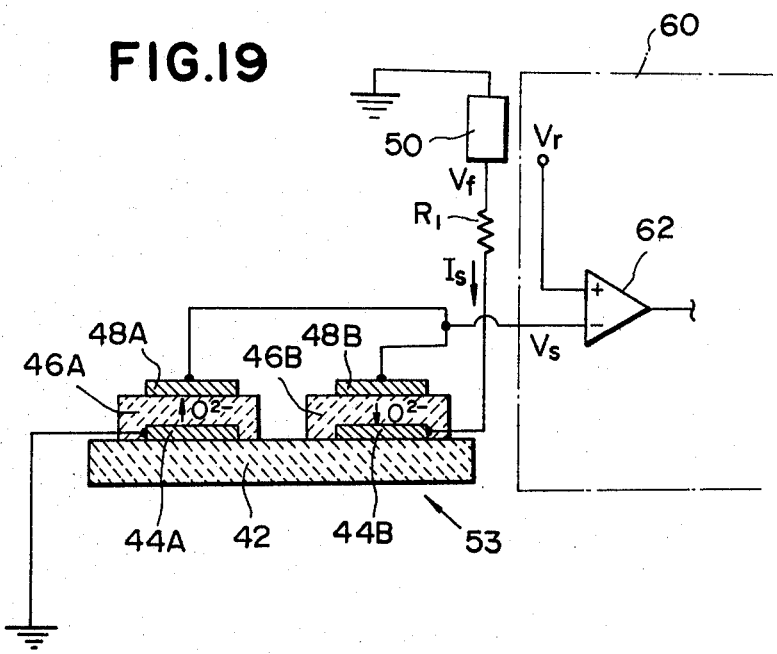

FIG. 19 shows still another embodiment of the invention. The device of FIG. 19 has an oxygen-sensitive element 53 which is identical in construction with the element 41 of FIG. 13. In this element 53, however, the two reference electrode layers 44A and 44B are not connected to each other and, instead, the first and second measurement electrode layers 48A and 48B are electrically connected to each other and connected to the negative input terminal of the comparator 62 of the signal-producing circuit 60. The source 50 of the constant DC voltage $V_f$ is connected to the second and first measurement electrode layers 48B and 48A such that a current $I_s$ flows through the second solid electrolyte layer 46B from the second measurement electrode 48B to the second reference electrode 44B and then through the first solid electrolyte layer 46A from the measurement electrode 48A to the reference electrode 44A. Accordingly, the directions of migration of oxygen ions in the respective solid electrolyte layers 46A and 46B become reversely of the ion-migration directions in the element 41 of FIG. 13.

Figure 20:
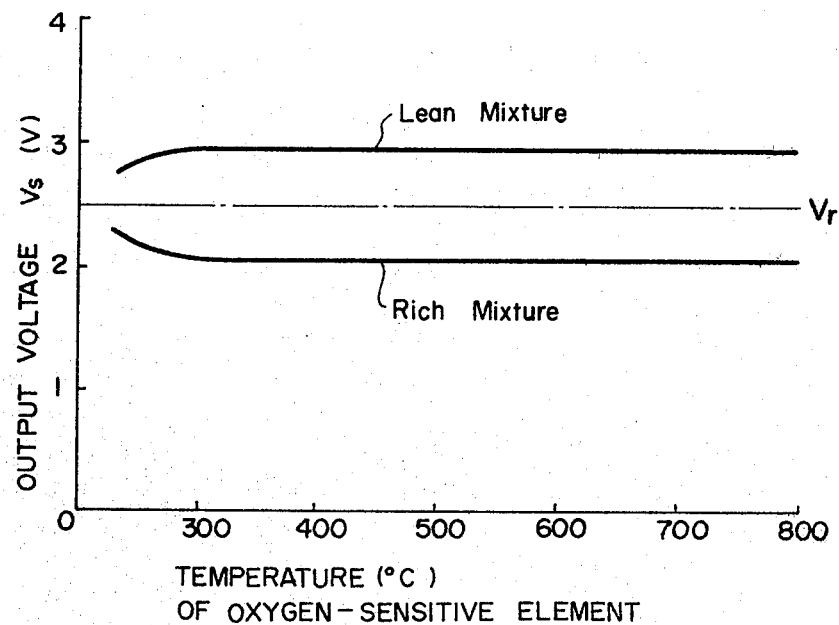
FIG. 20 is a graph similar to FIG. 12 but shows output characteristics of the device of FIG. 19.

Because of such modifications in electrical connections, output characteristics of this element 53 in exhaust gases of an internal combustion engine become as shown in FIG. 20, when the magnitude of the constant DC voltage $V_f$ is 5.0 V, in contrast to the output characteristics of the element 40 of FIG. 9 (or element 41 of FIG. 13) shown in FIG. 12. That is, the output voltage $V_s$ of this element 51 measured between the measurement and reference electrode layers 48A and 44A of the first cell becomes about 3 V while a lean mixture is supplied to the engine and about 2 V in the case of a rich mixture. In this case, therefore, the reference voltage $V_r$ is set at 2.5 V and applied to the positive input terminal of the comparator 62. In the device of FIG. 19, the comparator 62 produces an output voltage when the output voltage $V_s$ of the oxygen-sensitive element 53 is lower than the reference voltage $V_r$, that is, when the element 53 is exposed to an exhaust gas produced from a rich mixture. Accordingly, the signal-generating means (omitted from illustration in FIG. 19) of the circuit 60 and the fuel feed rate regulating means mentioned with reference to FIGS. 9 and 10 need no modification in the case of FIG. 19. If desired, however, it is permissible to apply the output voltage $V_s$ of the element 53 of FIG. 19 to the positive terminal of the comparator 62 and the reference voltage $V_r$ to the negative input terminal by modifying the relationship between the high and low levels of the control signal $S_c$ produced by the circuit 60 and the operation of the fuel feed rate regulating means.

Figure 21:
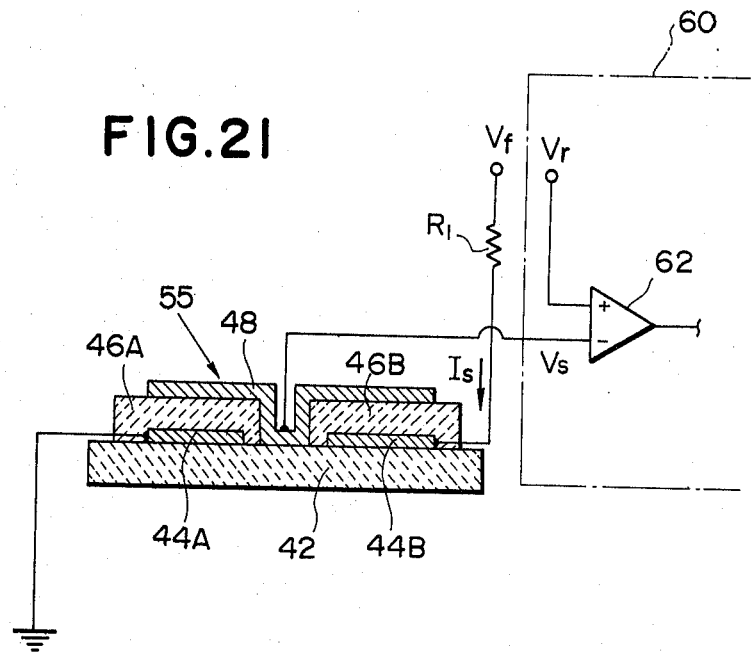
FIGS. 21–25 show five still differently designed devices embodying the present invention, respectively.

An oxygen-sensitive element 55 shown in FIG. 21 is generally similar to the element 53 of FIG. 19. As a sole modification, the first and second measurement electrode layers 48A and 48B in FIG. 19 are united into a single measurement electrode layer 48 in FIG. 21, which is connected to the negative input terminal of the comparator 62. Accordingly there is no difference in function between the two elements 53 and 55.

Figure 22:
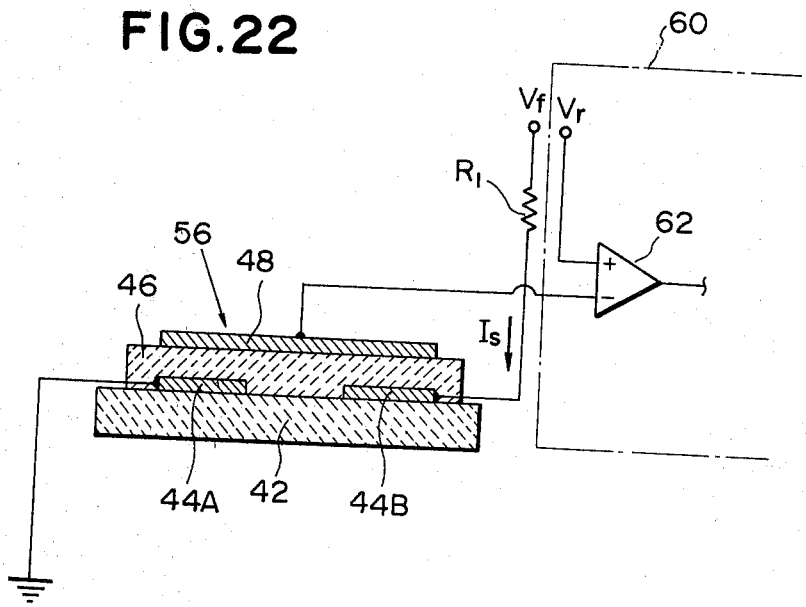

The element 55 of FIG. 21 may further be modified into an oxygen-sensitive element 56 shown in FIG. 22 by replacing the first and second solid electrolyte layers 46A and 46B by a single solid electrolyte layer 46 which is shared by the two oxygen concentration cells and laid with the single measurement electrode layer 48. In other respects these two elements 55 and 56 are identical.

Figure 23:
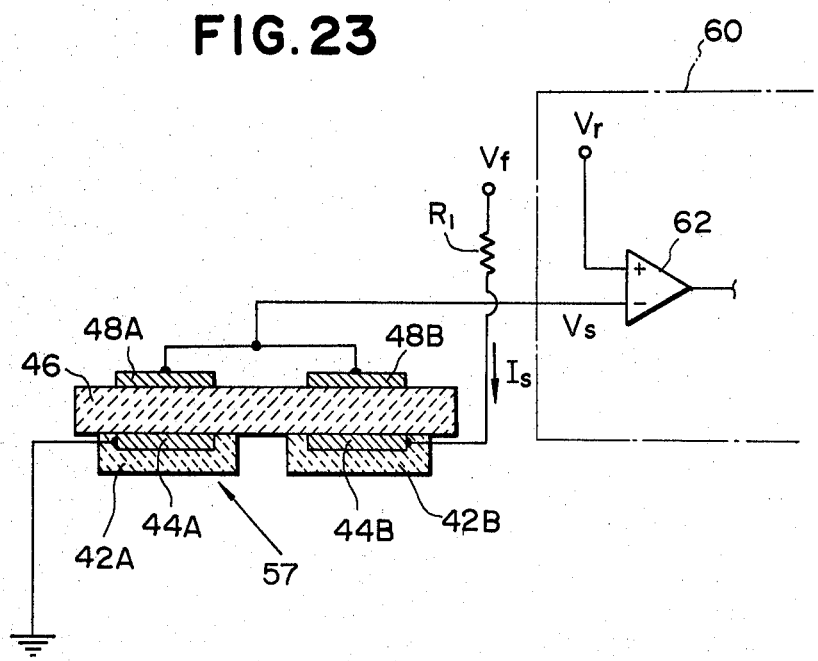

FIG. 23 shows an oxygen-sensitive element 57 having a single solid electrolyte layer 46, which is designed to serve as the substrate of this element 57 and carries thereon the first and second reference electrode layers 44A, 44B, first and second shield layers 42A, 42B and first and second measurement electrode layers 48A, 48B all formed and arranged similarly to the corresponding layers in the element 49 of FIG. 17. In electric connections, however, the element 57 of FIG. 23 is similar to the elements 53, 55, 56 of FIGS. 19, 21 and 22.

Figure 24:
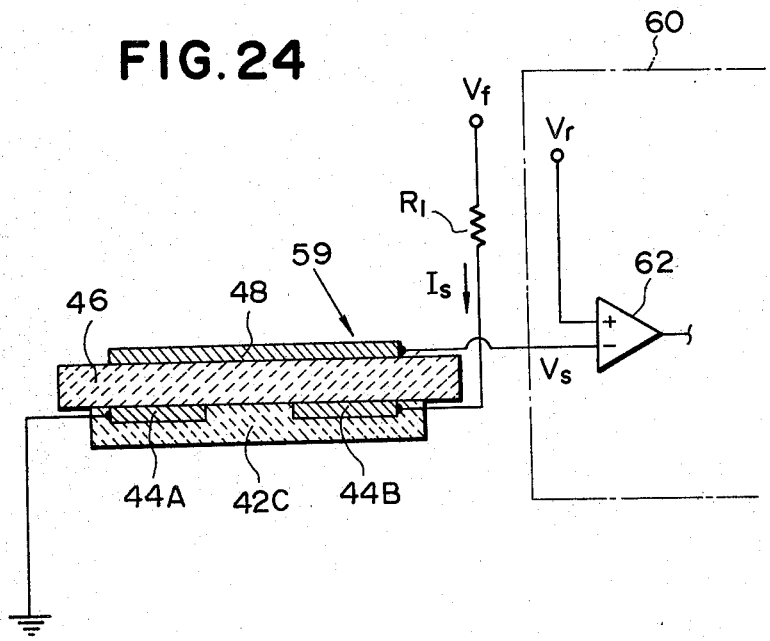
Figure 25:
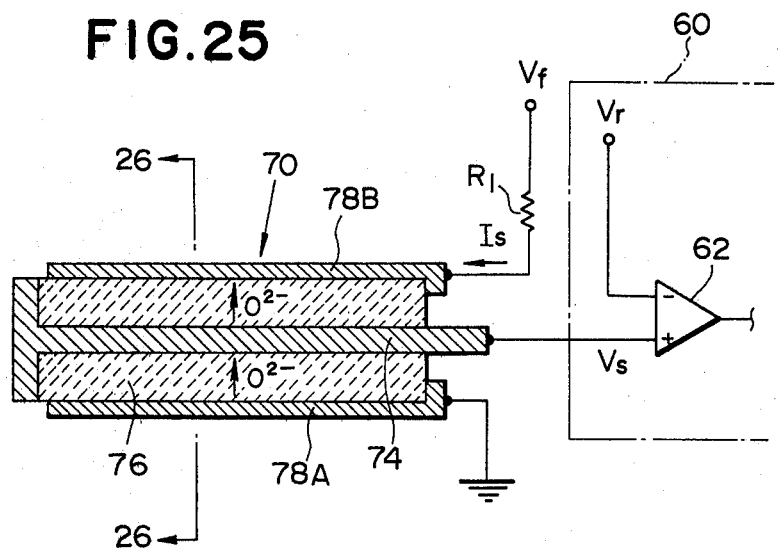
Figure 26:
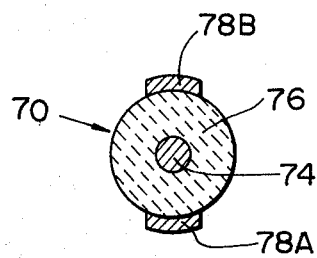
FIG. 26 is a cross-sectional view taken along the line 26—26 of FIG. 25.

The element 57 of FIG. 23 may be modified into an oxygen-sensitive element 59 shown in FIG. 24 by uniting the first and second measurement electrode layers 48A and 48B into a single measurement electrode layer 48 and, though optional, uniting the first and second shield layers 42A and 42B into a single shield layer 42C. There is no difference in function between these two elements 57 and 59.

Where it is intended to connect the first and second reference electrode layers 44A and 44B to each other or to unite these two electrode layers 44A, 44B into a single reference electrode layer 48, an oxygen-sensitive element according to the invention can be designed such that the solid electrolyte layer of each concentratin cell in the device serves also as the shield layer for the reference electrode layer of the other cell. FIGS. 25 and 26 show an oxygen-sensitive element 70 as an example of such design. A structurally basic member of this element 70 is a bar or rod 74 of an electronically conducting material, and this rod 74 is completely coated with a layer 76 of an oxygen ion conductive solid electrolyte substantially over the entire length. The solid electrolyte layer 76 is made to have a microscopically porous and gas permeable structure. On the outer surface of the solid electrolyte layer 76, gas permeably porous first and second measurement electrode layers 78A and 78B are formed at a distance therebetween. The rod 74 serves also as a single reference electrode of this element 70, so that an oxygen concentration cell is constituted of the reference electrode 74, the first measurement electrode layer 48A, and a portion of the solid electrolyte layer 76 intervening between these two electrodes 74 and 78A and another oxygen concentration cell constituted of the reference electrode 74, the second measurement electrode 78B and another portion of the solid electrolyte layer 76 intervening between these two electrodes 74 and 78B.

The rod-shaped single reference electrode 74 is connected to the positive input terminal of the comparator 62 in the signal-producing circuit 60, and the measurement electrode layers 78A and 78B are connected to the source of the constant DC voltage $V_f$ such that a DC current $I_s$ flows in the element 70 from the second measurement electrode layer 78B to the reference electrode 74 through the solid electrolyte layer 76 and then to the first measurement electrode layer 78A through the solid electrolyte layer 76. Accordingly, in a region between the first measurement electrode layer 78A and the reference electrode 74 oxygen ions migrate inwardly through the solid electrolyte layer 76, while in a region between the reference electrode 74 and the second measurement electrode layer 78B oxygen ions migrate outwardly through the solid electrolyte layer 76. Therefore, this oxygen-sensitive element 70 functions similarly to, for example, the element 47 of FIG. 16. A primary advantage of the oxygen-sensitive element 70 of FIGS. 25 and 26 is the possibility of easily producing a very small-sized element by using a thin wire, or a thin sheet metal, as the reference electrode 74. In practice, it is preferable to use a platinum wire as the reference electrode 74.

For every one of the oxygen-sensitive elements illustrated in FIGS. 9, 13-19 and 21-26, it is optional to provide a porous protective coating which covers the first and second measurement electrode layers 48A, 48B, 78A, 78B or the united measurement electrode layer 48, if desired together with the outer surfaces of the solid electrolyte layer(s), or even the entire outer surfaces of the element.

The material for each solid electrolyte layer 46, 46A, 46B, 46C, 76 can be selected from oxygen ion conductive solid electrolyte materials used for conventional oxygen sensors of the concentration cell type. Some examples are $ZrO_2$ stabilized with CaO, $Y_2O_3$, SrO, MgO, $ThO_2$, $WO_3$ or $Ta_2O_5$; $Bi_2O_3$ stabilized with $Nb_2O_5$, SrO, $WO_3$, $Ta_2O_5$ or $Y_2O_3$; and $Y_2O_3$ stabilized with $ThO_2$ or CaO. In the case of using the solid electrolyte layer 46 as the substrate of the oxygen-sensitive element as in FIGS. 17, 18, 23 and 24, this layer 46 may be produced, for example, by sintering of a press-moulded powder material or sintering of a so-called green sheet obtained by moulding or extrusion of a wet composition comprising a powdered solid electrolyte material as the principal component. Where the shield layer 46, or the electrode 74 as in FIG. 25, is used as the substrate of the oxygen-sensitive element, each solid electrolyte layer 46A, 46B, 46C, 76 may be formed as a thin film-like layer by a physical deposition technique such as sputtering or ion plating, or by an electrochemical technique typified by plating, or by a process having the steps of printing a paste containing a powdered solid electrolyte material onto the substrate and then firing the paste-applied substrate.

Each shield layer 42, 42A, 42B, 42C is usually made of an electrically insulating ceramic material such as alumina, mullite, spinel or forsterite, but, when the oxygen-sensitive element has a united reference electrode layer 44, optionally use may be made of a conducting material such as an elemental metal typified by platinum, an alloy such as stainless steel or a conducting cermet. When made to serve as the substrate of the oxygen-sensitive element, the shield layer 42 is produced, for example, by sintering of either a green sheet or a press-formed powder material, or by machining of a body of a selected material. Where the solid electrolyte layer 46 is used as the substrate, each shield layer 42A, 42B, 42C may be formed as a relatively thin film-like layer, for example, by a physical deposition technique, by plasma spraying or by the steps of printing a paste containing a powdered ceramic material onto the substrate and then sintering the printed paste layer.

Each of the reference and measurement electrode layers 44A, 44B, 44, 48A, 48B, 48 is made of an electronically conductive material selected from electrode materials for conventional solid electrolyte oxygen sensors. Examples are metals of the platinum group, which exhibit a catalytic action on oxidation reactions of hydrocarbons, carbon monoxide, etc., such as Pt, Pd, Ru, Rh, Os and Ir, including alloys of these platinum group metals and alloys of a platinum group metal with a base metal, and some other metals and oxide semiconductors such as Au, Ag, SiC, $TiO_2$, CoO and $LaCrO_3$ which do not catalyze the aforementioned oxidation reactions. Each electrode layer is formed on a shield layer or a solid electrolyte layer as a relatively thin film-like layer, for example, by a physical deposition technique such as sputtering or ion plating, or by an electrochemical technique typified by plating, or by printing of a paste containing a powdered electrode material, followed by firing of the paste-applied shield layer and/or solid electrolyte layer.

For the aforementioned porous protective coating, use may be made of a heat-resistant and electrically insulating material such as alumina, spinel, mullite or calcium zirconate ($CaO-ZrO_2$). The porous protective coating may be produced, for example, by plasma spraying or by the steps of immersing the oxygen-sensing element in a slurry of a selected powder material, drying the slurry adhered to the element and then firing the thus treated element.

What is claimed is:

1. A device to produce a control signal for feedback control of the air/fuel ratio of an air-fuel mixture supplied to a combustor, the device comprising:

an oxygen-sensitive element which is to be disposed in a combustion gas exhausted from the combustor and comprises two oxygen concentration cells each constituted of a layer of an oxygen ion conductive solid electrolyte, a measurement electrode layer formed on one side of the solid electrolyte layer, a reference electrode layer formed on the other side of the solid electrolyte layer and a shield layer provided on the reference electrode side of the solid electrolyte layer so as to closely cover the reference electrode layer, at least one of the solid electrolyte layer and the shield layer of each concentration cell having a microscopically porous and gas permeable structure, one of the measurement electrode layer and the reference electrode layer of one concentration cell being electrically connected to the corresponding one of the other concentration cell;

a constant voltage DC power source connected to the unconnected electrode layers of the respective concentration cells of the oxygen-sensitive element to force a DC current to flow through the solid electrolyte layers of the two concentration cells from the measurement electrode layer to the reference electrode layer in one cell and from the reference electrode layer to the measurement electrode layer in the other cell; and a signal-producing circuit having comparing means for making a comparison between a predetermined reference voltage and an output voltage of the oxygen-sensitive element developed between the measurement and reference electrode layers of a predetermined one of the two concentration cells to examine which one of the reference voltage and the output voltage is higher than the other and signal-generating means for producing a control signal which varies according to a high-low relationship between the reference voltage and the output voltage examined by the comparing means.

2. A device according to claim 1, wherein the shield layers of the two concentration cells are united into a single shield layer which is so shaped and dimensioned as to serve as a structurally basic member of the oxygen-sensitive element.

3. A device according to claim 2, wherein the solid electrolyte layers of the two concentration cells lie on two opposite sides of said single shield layer, respectively, such that the two cells are arranged generally symmetrically with respect to a middle plane in said single shield layer.

4. A device according to claim 3, wherein the solid electrolyte layers of the two concentration cells lie on the same side of said single shield layer such that the two cells are arranged generally symmetrically with respect to a plane perpendicular to said single shield layer.

5. A device according to claim 4, wherein the reference electrode layers of the two concentration cells are united into a single reference electrode layer.

6. A device according to claim 4, wherein the measurement electrode layers of the two concentration cells are united into a single measurement electrode layer.

7. A device according to claims 4, 5 or 6, wherein the solid electrolyte layers of the two concentration cells are united into a single solid electrolyte layer.

8. A device according to claim 1, wherein the solid electrolyte layers of the two concentration cells are united into a single solid electrolyte layer (46) which is so shaped and dimensioned as to serve as a structurally basic member of the oxygen-sensitive element.

9. A device according to claim 8, wherein the reference electrode layers of the two concentration cells are united into a single reference electrode layer.

10. A device according to claim 8, wherein the measurement electrode layers of the two concentration cells are united into a single measurement electrode layer.

11. A device according to claims 8, 9 or 10, wherein the shield layers of the two concentration cells are united into a single shield layer (42C).

12. A device according to claim 1, wherein the solid electrolyte layer of each one of the two concentration cells is made to serve also as the shield layer for the reference electrode layer of the other cell.

13. A device according to claim 12, wherein the reference electrode layers of the two concentration cells are united into a single reference electrode which is so shaped and dimensioned as to serve as a structurally basic member of the oxygen-sensitive element.

14. A device according to claim 13, wherein the solid electrolyte layers of the two concentration cells are united into a single solid electrolyte layer.

15. A device according to claim 1, wherein the signal-generating means of said circuit comprise a switching transistor the base of which is electrically connected to said comparing means such that an output voltage is provided from said comparing means to the base of said transistor when predetermined one of said reference voltage and said output voltage of said oxygen-sensitive element is higher than the other.

16. A device according to claim 15, wherein said signal-generating means comprise a voltage divider to which is applied a source voltage when said switching transistor is in the conducting state, said control signal being based on a voltage at an output terminal of said voltage divider.

* * * * *